US008690782B2

(12) United States Patent
Colby

(10) Patent No.: US 8,690,782 B2
(45) Date of Patent: Apr. 8, 2014

(54) SYSTEM FOR GENERATING MULTIPLE BEAMS FROM A SINGLE RECEIVE EVENT

(75) Inventor: Brian V. Colby, Renton, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1334 days.

(21) Appl. No.: 11/827,871

(22) Filed: Jul. 12, 2007

(65) Prior Publication Data

US 2009/0018443 A1 Jan. 15, 2009

(51) Int. Cl.
*A61B 8/00* (2006.01)

(52) U.S. Cl.
USPC .................. 600/447; 600/437; 600/443

(58) Field of Classification Search
None
See application file for complete search history.

(56) References Cited

U.S. PATENT DOCUMENTS

| | | | | |
|---|---|---|---|---|
| 4,136,325 A * | 1/1979 | Takamizawa et al. | .......... | 367/11 |
| 4,161,121 A * | 7/1979 | Zitelli et al. | .................... | 73/626 |
| 4,257,256 A * | 3/1981 | Yoshikawa | ....................... | 73/626 |
| 4,401,957 A * | 8/1983 | McKeighen et al. | ......... | 333/165 |
| 4,501,277 A * | 2/1985 | Hongo | ........................... | 600/441 |
| 4,581,636 A * | 4/1986 | Blaker et al. | .................. | 348/163 |
| 4,618,887 A * | 10/1986 | Birk | ............................... | 348/163 |
| 4,790,320 A * | 12/1988 | Perten et al. | .................. | 600/447 |
| 5,345,426 A * | 9/1994 | Lipschutz | ..................... | 367/103 |
| 5,345,939 A * | 9/1994 | Engeler et al. | ................ | 600/447 |
| 5,462,057 A * | 10/1995 | Hunt et al. | .................... | 600/447 |
| 5,469,851 A * | 11/1995 | Lipschutz | ..................... | 600/447 |
| 5,522,391 A * | 6/1996 | Beaudin et al. | ............... | 600/443 |
| 5,573,001 A | 11/1996 | Petrofsky et al. | | |
| 5,627,821 A * | 5/1997 | Miyagi | ......................... | 370/242 |
| 5,630,421 A * | 5/1997 | Barlow et al. | ................. | 600/459 |
| 5,722,412 A * | 3/1998 | Pflugrath et al. | .............. | 600/459 |
| 5,817,024 A * | 10/1998 | Ogle et al. | .................... | 600/447 |
| 5,891,038 A * | 4/1999 | Seyed-Bolorforosh et al. | .............................. | 600/447 |
| 5,905,692 A * | 5/1999 | Dolazza et al. | ............... | 367/123 |
| 5,961,460 A * | 10/1999 | Guracar et al. | ............... | 600/440 |
| 6,263,094 B1 * | 7/2001 | Rosich et al. | ................. | 382/128 |
| 6,352,511 B1 * | 3/2002 | Hossack et al. | ............... | 600/443 |
| 6,695,783 B2 * | 2/2004 | Henderson et al. | ........... | 600/443 |
| 6,773,399 B2 * | 8/2004 | Xi et al. | ......................... | 600/443 |
| 7,500,952 B1 * | 3/2009 | Chiang et al. | ................. | 600/446 |
| 7,540,842 B2 * | 6/2009 | Napolitano et al. | .......... | 600/443 |
| 7,682,309 B2 * | 3/2010 | Ji et al. | .......................... | 600/437 |
| 7,818,797 B1 * | 10/2010 | Fan et al. | ......................... | 726/22 |
| 2004/0002652 A1 | 1/2004 | Phelps et al. | | |
| 2008/0009725 A1 * | 1/2008 | Bae et al. | ....................... | 600/437 |
| 2008/0262351 A1 * | 10/2008 | Scampini | ...................... | 600/443 |

* cited by examiner

*Primary Examiner* — Long V. Le
*Assistant Examiner* — Angela M Hoffa

(57) ABSTRACT

A system and method for storing imaging information of multiple receive events and/or for generating a plurality of beams from a single receive event are disclosed. A transducer has a plurality of elements and is operable to receive a first acoustic signal from a first receive event and a second acoustic signal from a second receive event. A memory is in communication with the transducer to receive element data from the plurality of elements. The memory is operable in a first section and a second section. The memory is further operable to store first and second imaging data in the first and second sections, respectively. The first and second imaging data is based on the first and second acoustic signals, respectively.

24 Claims, 2 Drawing Sheets

SYSTEM FOR GENERATING MULTIPLE BEAMS FROM A SINGLE RECEIVE EVENT

BACKGROUND

The present invention relates to medical imaging. In particular, a system and method of storing multiple firings and generating multiple beams from imaging data from each of the receive events is provided.

Ultrasound technology is used for a variety of diagnostic and treatment purposes. For example, ultrasound images are relied on for monitoring fetal development, detecting abnormalities in tissue, or assisting medical professionals during invasive procedures, such as catheter localization. Two dimensional ("2D"), three dimensional ("3D"), and four dimensional ("4D") images (i.e., the fourth dimension is time, and, therefore, 4D images are a sequence of images that show an object over a time period) may be generated. The ultrasound images may show a variety of tissue and color information, such as B-mode (grey-scale) and Doppler information (e.g., motion or flow information).

Ultrasound images may be formed by beamforming. Generally, a transducer is utilized to transmit and receive the acoustic signals. The echo signals are converted into electrical energy to create images. For example, the transducer receives the echo signals to generate respective analog electrical signals. An analog-to-digital ("ADC") converter samples the analog electrical signals and provides the digital image information to delay memories corresponding to different channels. The respective delay memories delay the digital imaging information for each channel, and the delayed information is summed to form a beam for a respective scan line.

However, the generation of multiple beams from a single receive event is desired, especially for generation of 3D and 4D images. Known methods of generating multiple beams from a single receive event involves duplicating hardware. For example, multiple adders and delay calculators are used to generate multiple beams as imaging information is acquired from a single firing. As ultrasound systems are being reduced in size, less and less area is available for additional hardware. Also, smaller ultrasound systems relying on battery power may want to increase battery life by having less hardware.

BRIEF SUMMARY

By way of introduction, the preferred embodiments described below include an imaging system with a plurality of memories. Each of the memories is operable to store imaging information of separate receive events. Multiple beams may be generated from the stored imaging information of each single receive event.

According to a first aspect, a system for storing imaging information from multiple receive events is provided. A transducer has a plurality of elements and is operable to receive a first acoustic signal from a first receive event and a second acoustic signal from a second receive event. A memory is in communication with the transducer to receive element data from the plurality of elements. The memory is operable in a first section and a second section. The memory is further operable to store first and second imaging data in the first and second sections, respectively. The first and second imaging data is based on the first and second acoustic signals, respectively.

According to a second aspect, a system for generating multiple beams from a single receive event is provided. A plurality of transducer elements is provided. Each of the transducer elements is operable to receive first and second acoustic signals from first and second receive events, respectively. A plurality of memories are in communication with each of the transducer elements. The memories are further operable to store first and second imaging data. The first and second imaging data are based on the first and second acoustic signals, respectively. An adder is in communication with each of the memories. The adder is operable to generate a plurality of first beams based on stored first imaging data.

According to a third aspect, a method of generating multiple beams from a single receive event is provided. First and second acoustic signals from first and second receive events, respectively, are received. The first and second acoustic signals are converted into first and second imaging data, respectively. The first imaging data is stored in a first one of a plurality of memories. The second imaging data is stored in the first one of the plurality of memories. A plurality of first beams are generated based on the stored first imaging data.

According to a fourth aspect, a system for storing imaging information for multiple receive events is provided. A transducer has a plurality of elements. A receive beamformer is connected with the transducer. The receive beamformer comprises at least two delay memories. Each delay memory is operable to store information from an element for different receive events. An adder is connectable with the at least two delay memories. The adder is operable to sequentially form beams from the stored information in a first of the at least two delay memories.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A multiple buffer memory, such as a two port ping/pong memory, is used to store all of the ADC data for each receive event. An entire firing is captured prior to the beginning of or during the beamforming. Any number of beams can be generated sequentially from this data while another section or area of the ping/pong memory is available to receive data from the next receive event. For example, 128 beams may be sequentially generated for each firing from the same stored data while data for the next firing is being stored. For beamforming, software defines the address boundaries for different sections of the memory to identify data associated with the desired amount of delay for a particular beam. One copy of the beamforming hardware is used while retaining the ability to generate any number of beams depending on the exam type. Also, following the completion of a firing, the transducer through ADC chain can be powered down, reducing the power consumption of the system. For example, turning off a clock to beamforming hardware may be utilized for power saving once data is stored. Multiple beams can continue to be generated from the stored data.

Figure 1:
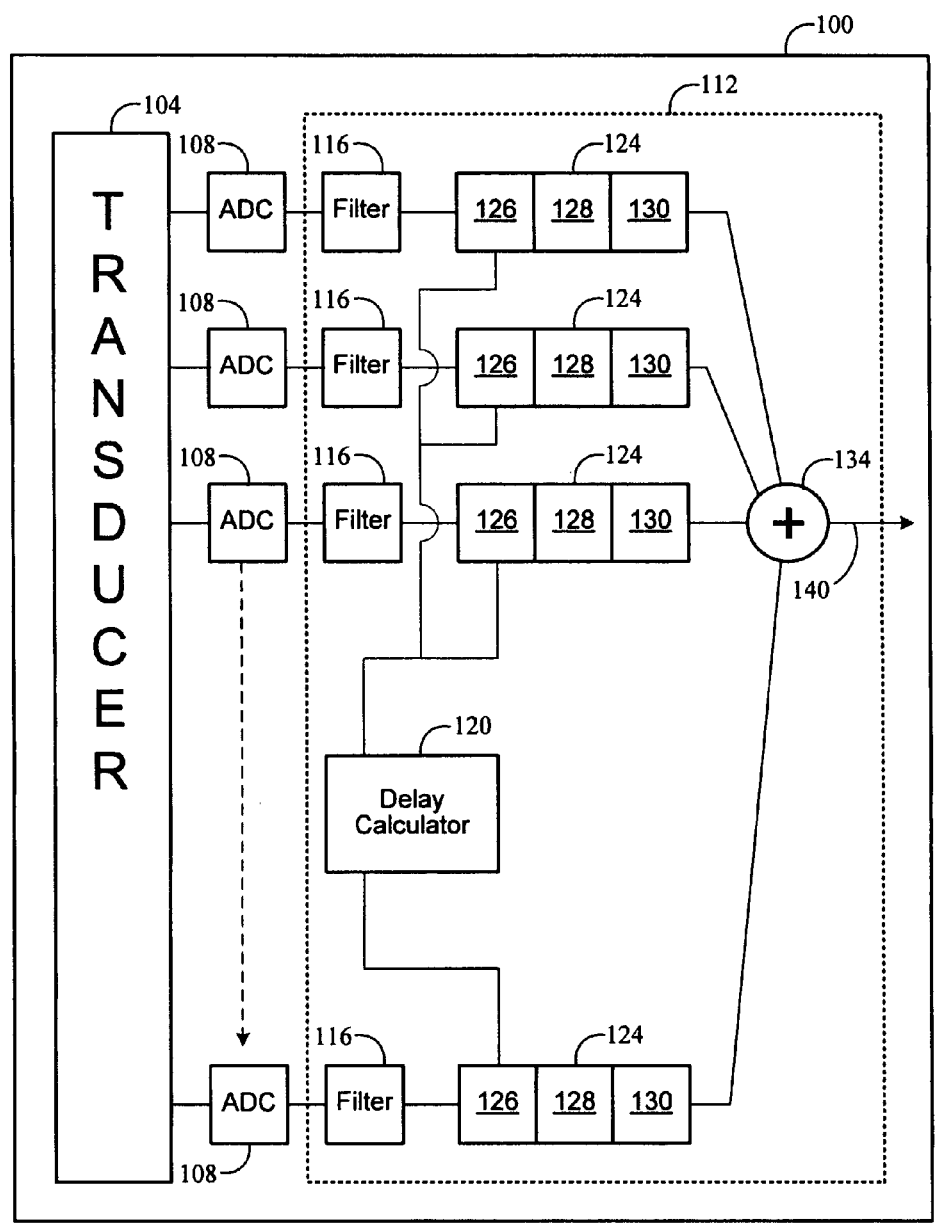
FIG. 1 is a diagram of one embodiment of an imaging system used for storing imaging information for multiple receive events and/or generating a plurality of beams.

FIG. 1 shows one embodiment of an imaging system 100. The imaging system 100 is an ultrasound system or any known or future medical or non-medical imaging system utilizing a transducer. Any ultrasound imaging system 100 may be used. In one embodiment, the imaging system 100 is a cart based imaging system. In another embodiment, the imaging system 100 is a portable system, such as a briefcase-sized system or laptop computer based system. Other embodiments include handheld ultrasound systems. For example, one or more housings are provided where the entire system is small and light enough to be carried in one or both hands and/or worn by a user. In another example, a transducer is in one housing to be held by a person, and the imaging components and display are in another housing to be held by a person. Coaxial cables connect the two housings. The entire handheld system weighs less than about 6 pounds, but may weigh more. For example, the handheld system weighs about 2 pounds or less. A single housing for an entire handheld system may be provided.

The imaging system 100 includes, but is not limited to, a transducer 104, analog-to-digital converters ("ADCs") 108, and a receive beamformer 112. Additional, different, or fewer components may be provided. For example, probe electronics, a transmit beamformer, an input device, write and read clocks, a display, an image processor, and additional memory may be provided. Also, the ADCs 108 may be a part of the receive beamformer 112. Any or all of the electronics may be integrated as one module, board, or chip.

The transducer 104 is a transducer array or a plurality of transducer arrays, such as a one dimensional linear phased transducer array or a multi-dimensional transducer array. The transducer 104, for example, is in an ultrasound probe connected with an ultrasound system. The transducer 104 is operable to receive acoustic signals and convert the acoustic signals into electrical energy. For example, the transducer 104 is operable to acquire ultrasound data by receiving echo signals. The ultrasound data includes Doppler, B-mode (greyscale), and other tissue or flow information.

The transducer 104 has a plurality of elements, such as about 64 or about 128 elements. However, any number of transducer elements may be used. The transducer elements are formed from transducer material. The transducer material is piezoelectric ("PZT"), ceramic, silicon, semiconductor and/or membrane, but other materials or structures may be used to convert between acoustical and electrical energies. For example, the transducer material is a single layer of transducer material or is a multi-layered transducer material having at least two layers of transducer material. Alternatively, the transducer material is a semiconductor substrate with one or more flexible membranes (e.g., tens or hundreds for each element) formed within or on the semiconductor substrate. The transducer elements may also include any number of different layers, such as matching layers, flex circuit layers, signal traces, electrodes, a lens and/or a backing block.

The ADCs 108 include any known or future analog-to-digital converters operable to sample analog signals, such as echo signals from tissue. For example, transistors coding different levels of an analog input waveform are provided. The ADCs 108 are in communication with the respective transducer elements (channels). The elements connect directly to the ADCs 108. Alternatively, multiplexers provide for aperture control to connect elements to different channels at different times. To reduce a number of cables, the number of connections from the elements to the ADCs 108 may be reduced. Time multiplexing, frequency multiplexing, sub-array mixing, partial beamforming or other processes for combining signals may be used. For example, signals from groups of four or other numbers of elements are combined onto common data paths by sub-array mixing, such as disclosed in U.S. Pat. No. 5,573,001 or U.S. Published Application No. 20040002652, the disclosures of which are incorporated herein by reference.

The receive beamformer 112 is in communication with the ADCs 108. Alternatively, the ADCs 108 are incorporated into the receive beamformer 112. The receive beamformer is an application specific integrated circuit ("ASIC"), processor, field programmable gate array ("FPGA"), analog components, digital components, integrated components, discrete devices, or combinations thereof. The receive beamformer includes, but is not limited to, filters 116, memories 124, a delay calculator 120, and an adder 134. Additional, different, or fewer components may be provided. For example, amplifiers may be provided for apodization. Any or all of the electronics may be integrated as one module, board, or chip.

In one embodiment, the filters 116 are in communication with the ADCs 108. The filters 116 act as decimation stages reducing the digital data sampled by the ADCs 108 to a shorter length or smaller size. The filters 116 may reduce data size about ten times. For example, 80 k of sampled data from one element is reduced to about 8 k. Alternatively, the filters 116 may reduce data to shorter or longer lengths or sizes. The filters 116 are finite impulse response ("FIR") digital filters, infinite impulse response ("IIR") digital filters, or any other known or future digital filter.

The memories 124 are in communication with the filters 116. For example, the memories 124 are implemented on a FPGA, such as an FPGA from the Altera Corporation. The memories may be other types, such as RAM memories. The memories are operable to store channel data and allow for delay for beamforming. For example, each of the memories 124 is a two port memory operable to store about 8 k of data. Alternatively, the memories include more than two ports and may store more or less data.

In one embodiment, each of the memories 124 is operable to be partitioned into multiple areas or sections for storing data of separate receive events. For example, the memories 124 are partitioned into sections 126, 128, and 130. The memories 124 may be partitioned into more or fewer sections. Software determines how many sections are to be provided and size of each of the sections during receiving operations. For example, when the imaging system 100 generates a transmit firing, the system knows, through processing logic, the type of information desired to be acquired, such as color or tissue information, the range or depth desired, as well as other parameters, and a section of the memory 124, such as the section 130, is reserved for the appropriate amount of data to be stored based on the transmit firing. Alternatively, all or some of the memories 124 are separate sections or partitions of a same device where the different areas or sections are for storing data of separate receive events.

A real time controller or processor may be used for partitioning the sections. For example, a look-up-table ("LUT") containing correlations between types and/or patterns of firings and partitioning of sections is provided. The correlations in the LUT are predetermined based on testing or are refreshed or updated substantially in real time during receive operations using extrapolation and/or interpolation techniques. The real time controller or processor partitions the memories 124 based on the present multiple firings and the LUT by retrieving the appropriate partitioning logic.

Therefore, when multiple transmit firings are generated, the memory 124 is partitioned into different sections based on the anticipated size of data to be received for each receive event. For example, if two successive receive events are anticipated to involve a large quantity of data each, then the memory may be partitioned into two sections. However, if three or more firings are generated and the respective anticipated receive events are to have a relatively small amount of data, then the memory 124 may be partitioned into three or more sections.

For example, the section 130 stores data from one receive event, the section 128 stores data from a second receive event, and the section 126 stores data from a third receive event. Each section stores element data for an entire scan. The memories 124 operate in a ping-pong fashion to store data from elements and read data out for beamforming. For example, as section 128 is being stored, stored data in section 130 is being outputted to form a beam. The same stored data may be used for sequentially forming receive beams along different scan lines. A section may be used to store only a part of an entire scan in other embodiments.

The delay calculator 120 is in communication with the memories 124 and is operable to assign delays to the stored data in the respective sections for forming beams along different scan lines. For example, as the section 128 is being stored, the delay calculator is assigning delays to each of the sections 130 to output data to the adder 134. The calculator determines the data or associated address corresponding to the desired delay for a given element. By reading out selected data associated with different delays or the desired time of receipt, data corresponding to a delay profile across the receive aperture is selected for output. The single adder 134 sums the delayed data to generate a beam 140 along a scan line. Therefore, one section is being read substantially at the same time as another section is being stored. The delay calculator sequentially or dynamically assigns respective delays to the stored data in the section 130 as the section 128 is being stored so that the adder sequentially generates a plurality of the beams 140, each along a different scan line. Data in one section (data from one receive event) may be used to form any number of beams. Without duplicating hardware, the data may be used sequentially to form one or more beams. For example, at least about 64 beams, such as about 128 beams, are sequentially generated. Fewer or more beams may be generated. Alternatively, multiple adders and delay calculators as well as other hardware may be used to generate beams substantially in parallel. The beams generated are provided to a backend of the imaging system 100, such as to a graphics video card or processor, to generate ultrasound images.

Timing of storing data in a section of the memories 124 and sequentially generating beams from stored data of another section of the memories 124 is considered. Software is programmed to control the rate of storage in the respective sections as well as the rate of generating beams to avoid interrupts. For example, stored data in the section 130 is being delayed to sequentially generate a plurality of the beams 140, and, at the same time, the section 126 and/or 128 are being stored. If the rate of storage of the section 126 or 128 is at a speed such that the data for the entire receive event being stored in section 126 or 128 is complete while the section 130 is still being used for generation of the beams 140, then an interrupt may occur if the section 130 is used to store new data from another receive event. Therefore, a balance of timing between storage rates, number of sections or memories (available memory) and generation rates is implemented via software or processor logic.

In an alternative embodiment, separate delay memories are used instead of the memories 124. For example, the sections 126, 128, and 130 are separate memories. The memories 126, 128, and 130 have a set maximum data storage capacity. The memories 126, 128, and 130 are in communication with the filters 116, the delay calculator 120, and the adder 134. Alternatively, additional adders and delay calculators as well as other hardware may be provided. A predetermined number of the memories is chosen for each channel. For example, three memories, such as the memories 126, 128, and 130, are chosen or only two memories, such as the memories 128 and 130, are utilized. Any number of separate memories may be used. The operation of the memories 126, 128, and 130 are substantially the same as the implementation discussed above. For example, two memories operate in a ping-pong fashion to store data from elements and read data out for beamforming. Each memory stores element data for an entire receive event. As one memory is storing, the other memory is outputting and an adder adds the information for beamforming. By reading data out of the memory from selected memory locations, data associated with different amounts of delay is provided. The same data may be used for sequentially forming receive beams along different scan lines for a same receive event.

In any embodiment, power saving operations are utilized during generation of beams. Clocks, such as write clocks, are shut off as well as other hardware after data is stored. For example, one or more of the sections or separate memories 126, 128, and 130 are full or not being used currently to further store data. While waiting for other actions or generation of beams from the stored data, write clocks, as well as power to the transducer 104, the ADCs 108, amplifiers, filters, and other receive and/or transmit hardware may be shut off to conserve power. The timing of shutting off power may be synchronized with the processing for triggering acoustic signals, storing data and partitioning memory, and generating beams along different scan lines.

Figure 2:
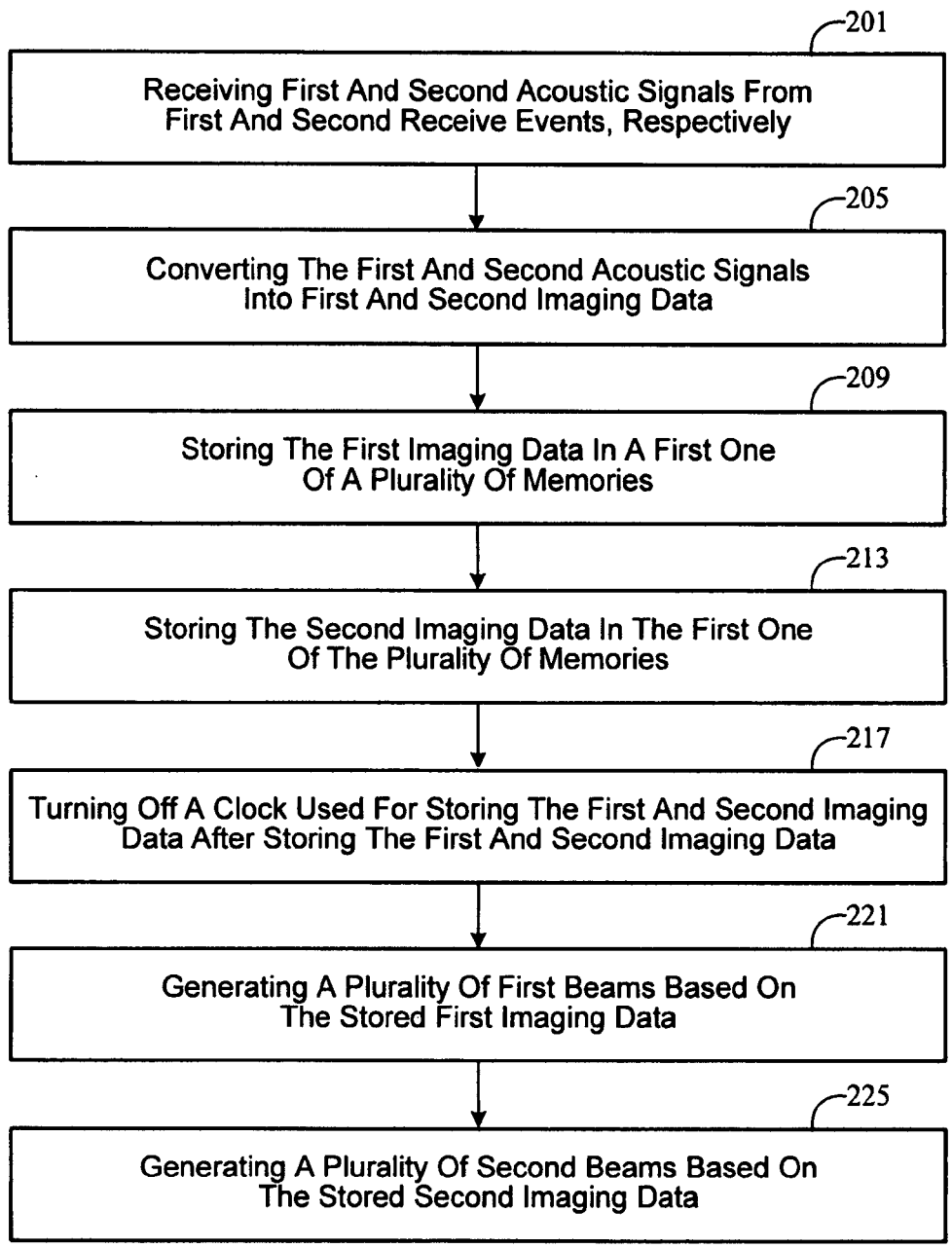
FIG. 2 is a flowchart of one embodiment of a method for generating a plurality of beams from a single receive event.

FIG. 2 is a flowchart of one embodiment of a method for generating a plurality of beams from a single receive event. Fewer or more acts may be provided. In act 201, first and second acoustic signals from first and second receive events are received, respectively. For example, multiple transmit firings of acoustic signals are generated by a transducer, such as the transducer 104. Each receive event includes respective acoustic echo signals that are received corresponding to each transmit firing. Acoustic signals are received at each element for a given receive event.

In act 205, the first and second acoustic signals received are converted into first and second imaging data. For example, the respective acoustic echo signals for each receive event are transduced into electrical energy by a plurality of elements of the transducer relating to different channels. The analog electrical signals for each channel are sampled by an ADC or a plurality of ADCs, such as the ADCs 108, to generate digital data. The digital data may be filtered to reduce the size of the data, such as by the filters 116.

In act 209, the first imaging data is stored in a first one of a plurality of memories, such as the memories 124. For example, data for an entire scan is stored in a section of each of the memories. The memories are partitioned into sections, such as the sections 126, 128, and 130, described above. Data, such as the first imaging data, is stored in one of the sections of each of the memories corresponding to a single receive event.

In act 213, the second imaging data is stored in the first one of the plurality of memories. For example, the second imaging data or other subsequent data of a different receive event is stored in another section of the memories. Software determines how many sections are to be provided and size of each of the sections during receiving operations. The determination is based on the type of information desired to be acquired, such as color or tissue information, the range or depth desired, as well as other parameters.

Alternatively, the imaging data is stored in separate memories instead of memories that are partitioned, as discussed above. For example, at least two memories are allocated for each channel. The at least two memories operate in a ping-pong fashion to store data from elements and read data out for beamforming. Each memory stores element data for an entire scan.

In act 217, power to hardware, such as a write clock, for storing data, such as the first and second imaging data, is turned or shut off after the storage of the data. For example, during generation of transmit firings and transducing of receive echoes of each receive event, power is supplied to the transducer and various electronics of the imaging system 100. Also, power to ADCs, filters, amplifiers, clocks, such as write clocks, is used to generate and store digital image data. To conserve power, power for write clocks, as well as power to the transducer, the ADCs, the amplifiers, the filters, and other receive and/or transmit hardware is shut off after the memories, such as the memories 124, are stored with data of separate receive events. While the mentioned circuitry is turned off, a plurality of beams along different scan lines are generated for each receive event based on the stored data. Alternatively, power to circuitry for storing data in a section of a memory or a separate memory may be shut off while another section or separate memory is being stored with data.

In act 221, a plurality of first beams, such as the beams 140, are generated based on the stored data, such as the first imaging data. The stored data is delayed by a delay calculator, such as the delay calculator 120, to match a scan line. The delayed output for each respective channel is summed by an adder, such as the adder 134, to form a beam. Alternatively, multiple adders in a pyramid or cascade arrangement may be used for forming a beam. Beams are sequentially generated based on the stored data for each receive event. Alternatively, multiple adders and delay calculators as well as other hardware may be used to generate beams substantially in parallel. At least about 64 beams, such as about 128 beams, are sequentially generated. Fewer or more beams may be generated. As beams are being generated from one section or separate memory with stored data, such as the first imaging data of act 209, data, such as the second imaging data of act 213, is being stored in another section or separate memory. Alternatively, beams are generated from respective sections or memories after storage of all data of multiple receive events.

For example, in act 225, a plurality of second beams are generated based on stored data, such as the second imaging data of act 213, after beams have been generated from data of another section or separate memory, such as the first imaging data. Also, the second beams are generated while another section or separate memory, such as the section or separate memory that stored the first imaging data, is being stored with data of a different third receive event. Alternatively, the second beams are generated from respective sections or memories after storage of all data from multiple receive events.

Any number of sections within a plurality of memories or separate memories may be used to store data of a complete scan of separate receive events. The stored data is used to generate multiple beams along different scan lines for each receive event. The beams are transmitted to a video or graphics processor to generate 2D, 3D, and/or 4D ultrasound images. The images are displayed on a liquid crystal display, ("LCD"), printer, or cathode ray tube ("CRT") monitor for viewing.

The imaging system 100 includes instructions that can be executable by a processor. The instructions are stored in a computer-readable medium. The instructions implement the methods, acts, and processes described above. The instructions for implementing the processes, methods and/or techniques discussed above are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system. Also, any of the features, methods, techniques described may be mixed and matched to create different systems and methodologies.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A system for storing imaging information from multiple receive events, the system comprising:
   a transducer having a plurality of elements and configured to receive a first acoustic signal from a first receive event and a second acoustic signal from a second receive event, the second receive event occurring after the first receive event and the first and second receive events being in response to first and second successive transmit firings, respectively; and
   a memory in communication with the transducer to receive element data from the plurality of elements, the memory configured in a first section and a second section,
   the memory further configured to store first and second imaging data in the first and second sections, respectively, the first and second imaging data based on the first and second acoustic signals, respectively, received by at least one of the same elements at different times, the first section configured to store the first imaging data and not the second imaging data, and the second section configured to store the second imaging data and not the first imaging data;
   wherein the first and second receive events comprise reception of the first and second acoustic signals for a full scan depth in response to the first and second transmit firings, respectively, the first and second receive events each being for separate reception along the full scan depth in succession such that an adder is configured to generate first beams while the second imaging data from the second receive event is being stored, and configured to then generate second beams from the second imaging data while the first imaging data is replaced by third imaging data associated with a third transmit firing.

2. The system of claim 1, wherein memory is configured such that the first imaging data is read from the first section substantially at the same time as when the second imaging data is being stored in the second section.

3. The system of claim 1, wherein the transducer and the memory are part of a handheld ultrasound system.

4. The system of claim 3, wherein the handheld ultrasound system weighs less than about six pounds.

5. The system of claim 3, wherein the handheld ultrasound system weighs about two pounds or less.

6. The system of claim 1, wherein the memory comprises a two port memory.

7. The system of claim 1, wherein the memory is further configured to delay output of the stored first and second imaging data for beamforming.

8. A system for generating multiple beams from a single receive event, the system comprising:
- a plurality of transducer elements, each of the transducer elements operable to receive first and second acoustic signals from first and second receive events, respectively, the second receive event occurring after the first receive event and the first and second receive events being in response to first and second successive transmit firings, respectively;
- memory groups each comprising a plurality of memories, each of the memory groups in communication with a respective one of the transducer elements;
- each of the memory groups further configured to store first and second imaging data, the first and second imaging data based on the first and second acoustic signals, respectively, received by at least one of the same elements at different times, a first memory in each memory group configured to store the first imaging data and not the second imaging data, and a second memory in each memory group configured to store the second imaging data and not the first imaging data; and
- an adder in communication with each of the memories, the adder configured to generate a plurality of first beams based on stored first imaging data and generate a plurality of second beams based on stored second imaging data;
- wherein the first and second receive events comprise reception of the first and second acoustic signals for a full scan depth in response to the first and second transmit firings, respectively, the first and second receive events each being for separate reception along the full scan depth in succession such that the adder is configured to generate the first beams while the second imaging data from the second receive event is being stored, and configured to then generate the second beams from the second imaging data while the first imaging data is replaced by third imaging data associated with a third transmit firing.

9. The system of claim 8, wherein the memories are configured such that the first imaging data is read from the memories substantially at the same time as when the second imaging data is being stored in the memories.

10. The system of claim 8, wherein the adder is further configured to generate the plurality of the second beams based on the stored second imaging data sequentially with the generation of the first beams.

11. The system of claim 8, wherein the plurality of first beams comprises at least sixty four beams.

12. The system of claim 8, further comprising:
- a delay calculator in communication with each of the memories.

13. The system of claim 8, further comprising:
- a plurality of analog-to-digital converters in communication with the plurality of transducer elements, respectively.

14. The system of claim 8, wherein the plurality of transducer elements and the memory groups are part of a handheld ultrasound system.

15. The system of claim 14, wherein the handheld ultrasound system weighs less than about six pounds.

16. A method of generating multiple beams from a single receive event, the method comprising:
- receiving first and second acoustic signals from first and second receive events, respectively;
- converting the first and second acoustic signals into first and second imaging data, respectively;
- storing the first imaging data in a first one of a plurality of memories;
- storing the second imaging data in the first one of the plurality of memories;
- generating a plurality of first beams based on the stored first imaging data, the first beams formed from the stored first imaging data from the first one of the memories; and
- generating a plurality of second beams based on the stored second imaging data, the second beams formed from the stored second imaging data from the first one of the memories;
- wherein generating the plurality of the first beams comprises generating the plurality of first beams from the first imaging data of the first receive event when storing the second imaging data;
- wherein receiving comprises receiving with the first and second receive events comprising reception for a full scan depth in response to the first and second transmit firings, respectively, and wherein generating the first and second beams comprises generating the first beams while the second imaging data from the second receive event is being stored and generating the second beams from the second imaging data while the first imaging data is replaced by third imaging data associated with a third transmit firing.

17. The method of claim 16, wherein generating the plurality of the first beams comprises generating at least sixty four first beams.

18. The method of claim 16, further comprising:
- using a clock in storing the first and second imaging data;
- turning off the clock used for storing the first and second imaging data after storing the first and second imaging data.

19. The method of claim 16, wherein generating the plurality of the first beams comprises generating the plurality of first beams using a single adder.

20. The method of claim 16, wherein generating the second beams occurs when storing third imaging data in the first one of the plurality of memories, the third imaging data based on a third acoustic signal from a third receive event.

21. The method of claim 16, wherein storing the first imaging data comprises partitioning the first one of the plurality of memories to include a first section based on a size of the first imaging data.

22. A system for generating multiple beams from a single receive event, the system comprising:
- a transducer having a plurality of elements; and a receive beamformer connected with the transducer, the receive beamformer comprising:

at least two delay memories, each delay memory configured to store information from an element for different receive events, the different receive events separate in time; and an adder configured to connect with the at least two delay memories, the adder configured to sequentially form beams from the stored information in the at least two delay memories such that the adder is configured to form the beams for one of the different receive events while the information for another one of the different receive events is being stored in the at least two delay memories;

wherein the information from different receive events comprises information from reception of first and second acoustic signals for a full scan depth in response to first and second transmit firings, respectively, the different receive events each being for separate reception along the full scan depth in succession such that the adder is configured to generate first beams while the information from a different one of the receive events is being stored and configured to then generate second beams while the information used for the first beams is replaced by additional information from another different receive event associated with a third transmit firing.

23. The system of claim 22, wherein the adder is configured to form at least sixty four beams from the information from the element in a first of the at least two delay memories, and then form at least sixty four more beams from the information from the element in a second of the at least two delay memories.

24. The system of claim 23, wherein the receive beamformer is configured to store the information in the first of the at least two delay memories while the adder adds the information in the second of the at least two delay memories.

* * * * *